United States Patent
Trahan

(10) Patent No.: US 10,987,286 B2
(45) Date of Patent: Apr. 27, 2021

(54) HAIR COMPOSITIONS AND METHODS OF USE THEREOF

(71) Applicant: Living Proof, Inc., Boston, MA (US)

(72) Inventor: Lauren A. Trahan, Andover, MA (US)

(73) Assignee: Living Proof, Inc., Boston, MA (US)

( * ) Notice: Subject to any disclaimer, the term of this patent is extended or adjusted under 35 U.S.C. 154(b) by 0 days.

(21) Appl. No.: 15/540,581

(22) PCT Filed: Jan. 8, 2016

(86) PCT No.: PCT/US2016/012693
§ 371 (c)(1),
(2) Date: Jun. 29, 2017

(87) PCT Pub. No.: WO2016/112320
PCT Pub. Date: Jul. 14, 2016

(65) Prior Publication Data
US 2018/0000699 A1      Jan. 4, 2018

Related U.S. Application Data

(60) Provisional application No. 62/101,651, filed on Jan. 9, 2015.

(51) Int. Cl.
*A61K 8/04* (2006.01)
*A61K 8/34* (2006.01)
*A61Q 5/06* (2006.01)
*A61K 8/81* (2006.01)
*A61K 8/02* (2006.01)

(52) U.S. Cl.
CPC ............ *A61K 8/046* (2013.01); *A61K 8/0279* (2013.01); *A61K 8/34* (2013.01); *A61K 8/8152* (2013.01); *A61Q 5/06* (2013.01); *A61K 2800/31* (2013.01); *A61K 2800/412* (2013.01)

(58) Field of Classification Search
None
See application file for complete search history.

(56) References Cited

U.S. PATENT DOCUMENTS

| | | | |
|---|---|---|---|
| 5,534,348 A * | 7/1996 | Miller | B01J 13/043 428/402 |
| 5,637,291 A | 6/1997 | Bara et al. | |
| 5,914,117 A | 6/1999 | Lavaud | |
| 6,403,070 B1 | 6/2002 | Pataut et al. | |
| 7,998,465 B2 | 8/2011 | De La Poterie et al. | |
| 2002/0034486 A1 | 3/2002 | Midha et al. | |
| 2003/0086886 A1 | 5/2003 | Midha | |

(Continued)

FOREIGN PATENT DOCUMENTS

| | | |
|---|---|---|
| CN | 101795661 A | 8/2010 |
| EP | 2033618 A1 | 3/2009 |

(Continued)

OTHER PUBLICATIONS

Araujo et al. (Polymer Engineering and Science, Jul. 1, 2002).*

(Continued)

*Primary Examiner* — Bong-Sook Baek
(74) *Attorney, Agent, or Firm* — McCarter & English, LLP; Michael J. DeGrazia

(57) ABSTRACT

Hair spray compositions comprising a liquid carrier, hollow, fluid-filled micropspheres, a polymer fixative, and propellant are provided.

21 Claims, 3 Drawing Sheets

(56) References Cited

U.S. PATENT DOCUMENTS

| | | |
|---|---|---|
| 2003/0086896 A1 | 5/2003 | Midha et al. |
| 2004/0228886 A1* | 11/2004 | Ding ............ A61K 8/0283 424/401 |
| 2005/0118126 A1 | 6/2005 | Rollat et al. |
| 2006/0083762 A1 | 4/2006 | Brun et al. |
| 2009/0061004 A1 | 3/2009 | Birkel et al. |
| 2009/0285866 A1* | 11/2009 | Afriat ................ A61K 8/31 424/401 |
| 2011/0067720 A1* | 3/2011 | Ranade .............. A61K 8/11 132/202 |
| 2013/0280174 A1 | 10/2013 | Lipic et al. |
| 2015/0007849 A1* | 1/2015 | Cajan ................ A61Q 5/06 132/203 |

FOREIGN PATENT DOCUMENTS

| | | |
|---|---|---|
| JP | 2005-126438 A | 5/2005 |
| JP | 2012-236804 A | 12/2012 |
| WO | 2001/74311 A2 | 10/2001 |
| WO | 03/028678 A1 | 4/2003 |
| WO | 2009/027943 A2 | 3/2009 |
| WO | 2013/034527 A2 | 3/2013 |

OTHER PUBLICATIONS

Akzo Nobel: "Product Specification for Expancel Microspheres: Expancel DU," Expancel Microspheres: An Introduction, Issue Mar. 2011.Jan. 1, 2011 (2 pages).

Anonymous: "Natpure Hollowbead | Adina," Retrieved from the Internet on Mar. 1, 2016: <http://www.cosmeticingredients.co.uk/ingredient/natpure-hollowbead>. (2 pages).

* cited by examiner

HAIR COMPOSITIONS AND METHODS OF USE THEREOF

RELATED APPLICATIONS

This application is a 35 U.S.C. § 371 national stage filing of International Application No. PCT/US2016/012693, filed Jan. 8, 2016, which claims the benefit of U.S. Provisional Patent Application No. 62/101,651, filed Jan. 9, 2015. The entire contents of each of the aforementioned applications are hereby incorporated by reference.

BACKGROUND

"Flat" or "limp" are common complaints for consumers with fine, thin hair. To improve their satisfaction with their hair, consumers desire more volume: increasing the space the hair occupies, making the hair appear more bulky and full. There are many factors that influence hair volume: the total number of hair fibers, the hair diameter, and hair fiber-to-fiber interactions are key factors.

In an attempt to increase hair volume, styling polymers have been used to alter fiber-to-fiber interactions and lock in the volume. These fiber-fiber bonds can be easily broken from external stresses, such as brushing or running fingers through the hair, resulting in a decrease in volume. Such styling polymers may also result in stiff-looking hair or exhibit polymer flaking after application to the hair. Other products incorporate solid particles to increase the perceived diameter of the hair fiber and or increase friction to make individual hair fibers look and feel thicker. However, solid particles used in these hair products can be heavy, and, while an initial boost in volume occurs, such components weigh the hair down over time.

Therefore, there remains a need for a hair treatment that increases the volume of the hair on a subject without the disadvantage of incorporating materials that counteract the volume increase over time and or have a poor tactile feel.

SUMMARY OF INVENTION

Distinct challenges existed in incorporating fluid-filled particles (e.g., microspheres) into anhydrous (e.g., ethanol) based systems, specifically aerosols, prior to the invention disclosed herein. First, the particles are insoluble and need be suspended uniformly throughout the composition. In aqueous based systems, numerous viscosity modifying agents are available to hold the fluid-filled particles in suspension to ensure uniform application by the consumer. However, there are significantly less viscosity modifiers available for anhydrous systems. As the viscosity of the system needs to be low enough so the composition can be sprayed without clogging the delivery device, but high enough to keep the fluid-filled microspheres in suspension long enough to achieve uniform application, having less options for the viscosity modifying agents for an anhydrous system was an obstacle. Additionally, an aerosol delivery system of fluid-filled particles posed safety challenges due to risk of inhalation exposure.

The present invention is a hair composition that surprisingly increases the volume of hair on a subject. In a first embodiment, the invention is a hair composition that includes at least one liquid carrier; hollow, fluid-filled microspheres; at least one hair-fixing polymer, and at least one propellant. In a second embodiment, the invention is a hair treatment composition packaged in an aerosol device comprising at least one liquid carrier; hollow, fluid-filled microspheres; at least one polymer fixative, and at least one propellant. In a third embodiment, the invention is an aerosol hair spray composition comprising at least one liquid carrier; hollow, fluid-filled microspheres; at least one polymer fixative, and at least one propellant. In a fourth embodiment, the invention is an aerosol, essentially anhydrous hair spray composition comprising at least one liquid carrier; hollow, fluid-filled microspheres; at least one polymer fixative, and at least one propellant.

The hair composition of the present invention deposits the hollow, fluid-filled microspheres along the hair shaft, between the hair fibers. A low level of resin is used to adhere the microspheres to the hair fiber. These microspheres are large enough to prevent adjacent hair fibers from coming in direct contact with each other, creating gaps between fibers to give the appearance of thicker, more voluminous hair. Additionally, the microspheres have a lower density than conventional powders, which prevents them from weighting the hair down over time, resulting in volume failure. Moreover, the hair composition of the present invention also adds a textured feel to hair. By increasing the texture on the hair fiber surface, consumers have a tactile sensation that their hair is thicker and fuller.

The present invention leverages the use of hollow, fluid-filled microspheres in an essentially anhydrous, aerosol delivery system to improve the appearance of volume in hair as well as alter the tactile sensation so that the hair feels thicker.

BRIEF DESCRIPTION OF THE DRAWINGS

Further objects and advantages of the disclosure will become apparent from the following description and from the accompanying drawings, wherein.

DETAILED DESCRIPTION

Figure 1:
FIG. 1 is photograph of mannequin head onto which a composition of the invention was applied to the right side of the mannequin's head and a control composition was applied to the left side.

The composition of the present invention includes a liquid carrier, hollow, fluid-filled microspheres, a polymer fixative, and propellant. In one embodiment of the invention, the compositions are in the form of aerosolized liquids. In one embodiment of the invention, the compositions are in the form of essentially anhydrous, aerosolized liquids.

Liquid Carrier:

The composition comprises a liquid carrier, which is present at a level from about 2% to 50% of the formula, preferably from about 2% to 20%, by weight of the composition. The liquid carrier is a volatile alcohol but may include a low level of water or other solvents, especially to comply with regional volatile organic compound (VOC)

restrictions. Volatile alcohols include monohydric alcohols having 1 to 6 carbons, preferably ethanol and isopropanol, more preferably ethanol.

Hollow, Fluid-Filled Microspheres

Fluid-filled microspheres consist of a hollow shell, typically constructed using either a polymer or glass. As used herein, a "microsphere" is a particle of any geometric shape (i.e., a sphere, a cylinder, a cube, an ovoid, etc. or of an irregular shape). The term "fluid" as used herein, means a liquid or a gas which tends to take the shape of its container, container being the wall of the flexible microspheres. The shell is filled with a liquid or gas, typically air or a hydrocarbon like isobutane. When heated, the pliable and non-rigid shell softens and the fluid inside expands (liquid to gas, gas to expanded gas), resulting in a sphere that expands like a balloon up to as much as four times its initial size (see https://www.akzonobel.com/expancel/knowledge_center/tutorials/one/ for additional information, the teachings of which are herein incorporated by reference). After the heat source is removed, the shell stays in its deformed/expanded state.

In some embodiments, the microspheres used in the present composition are expanded prior to inclusion in the present composition. In particular, the microspheres used in the present invention are expanded with heat prior to combination with the other components of the compositions described herein. As such, no further heat is needed to expand the microspheres, and the microspheres will provide an instant volumizing effect upon application to the hair.

The polymer is typically a thermoplastic polymer. In some embodiments of the invention, the microspheres comprise a thermoplastic material wall. In particular, the thermoplastic material is a polymer or copolymer of at least one monomer selected from the group consisting of acrylates, methacrylates (for example, methylacrylates) styrene, substituted styrene, unsaturated dihalides (for example, 1,1-dichloroethene (also referred to as vinylidene chloride), acrylonitriles, methacrylonitriles, vinyl and vinyl chloride. In a specific embodiment, the thermoplastic material is a acrylonitrile/methyl methacrylate/vinylidene chloride copolymer. In another specific embodiment, the thermoplastic material is an acrylonitrile/methacrylonitrile/methyl methacrylate copolymer. In another specific embodiment, the thermoplastic material is an acrylonitrile/methyl methacrylate copolymer.

In another aspect, the fluid-filled microsphere comprises a copolymer of either Acrylonitrile/Methyl Methacrylate/Vinylidene Chloride Copolymer, Acrylonitrile/Methacrylonitrile/Methyl Methacrylate Copolymer, or equivalent thermoplastic copolymer, such as that sold under the tradename EXPANCEL® by Akzo Nobel. In one embodiment, EXPANCEL® 461 DE 20 d70 (Acrylonitrile/Methyl Methacrylate/Vinylidene Chloride Copolymer, Isobutane), EXPANCEL® 461 WEP 20 d36 (acrylonitrile/methyl methacrylate/vinylidene chloride copolymer), or EXPANCEL® 551 DE 40 d42 (Acrylonitrile/Methyl Methacrylate/Vinylidene Chloride Copolymer, Isobutane), each made from a copolymer of acrylonitrile, methyl methacrylate and vinylidene chloride monomers can be used as the fluid-filled microsphere.

In one embodiment, EXPANCEL® 920 DU 80 (Acrylonitrile/Methacrylonitrile/Methyl Methacrylate Copolymer, Isobutane) and EXPANCEL® 920 WEP (Acrylonitrile/Methacrylonitrile/Methyl Methacrylate Copolymer, Isobutane), each made from a copolymer of acrylonitrile, methacrylonitrile and methyl methacrylate monomers can be used as the fluid-filled microsphere.

In one embodiment, EXPANCEL® FG52 DU 80 (Acrylonitrile/Methyl Methacrylate Copolymer, Isobutane), made from a copolymer of acrylonitrile and methyl methacrylate monomers can be used as the fluid-filled microsphere.

In another aspect, the fluid-filled microsphere comprises a polymer shell consisting of either acrylonitrile copolymer or polyvinylidene chloride copolymer with a calcium carbonate coating, such as that sold under the tradename Dualite® polymeric microspheres by Henkel. In one embodiment, Dualite® E135-040D (Acrylonitrile Copolymer, Calcium Carbonate) or Dualite® E130-055D (Polyvinylidene Chloride Copolymer, Calcium Carbonate) can be used as the fluid-filled microsphere. Other Dualite® microspheres with a larger particle size can be used, however, such microspheres may be visible on the hair. To reduce the visibility of the larger-sized microspheres, such microspheres could be coated with a coloring agent or an agent that modifies the refractive index to reduce the visibility of the microsphere on hair.

In another aspect, the fluid-filled microsphere comprises a glass shell, such as that sold under the tradename Hollow Glass Microspheres from Cospheric. In one embodiment, Hollow Glass Microsphere HGMS-0.36 27-32 μm (Sodium Silicate, Sodium Borate) can be used as the fluid-filled microsphere.

In another aspect, the fluid-filled microsphere comprises a glass shell such as that sold under the tradename Q-Cel® and Sphericel® Hollow Glass Microspheres from Potters Industries. In one embodiment, Sphericel® 45P25 (Sodium Borosilicate) can be used as the fluid-filled microsphere.

In another aspect, the fluid-filled microsphere comprises a glass shell, such as that sold under the tradename 3M Glass Bubbles® from 3M, or any other hollow microsphere. In one embodiment, 3M Glass Bubble® iM30K (Soda Lime Borosilicate Glass) can be used as the fluid-filled microsphere.

In another embodiment, the thermoplastic material is a copolymer that is essentially free of residual starting materials. "Essentially free of residual starting materials" includes polymers that meet safety and regulatory requirements in the cosmetics industry. Removal of residual starting materials is beneficial as some starting materials may be an inhalation hazard and accordingly, their presence in an aerosolized spray should be avoided or reduced. "Essentially free of residual starting materials" also means that after the polymerization reaction is complete, the resulting polymer contains less than about 0.01% of any of the residual starting materials. A "residual starting material" includes any remaining unreacted monomer used in preparing the polymer. In one embodiment, the resulting polymer contains less than about 0.01%; about 0.001%; about 0.0001%; about 0.00001% of any one of the residual starting materials, wherein any one of these values can be an upper or a lower limit of the range.

Residual starting materials include, for example, acrylonitrile, methacrylonitrile, acrylamide, butadiene, methyl methacrylate, and vinylidene chloride. In some embodiments, "essentially free of residual starting materials" means that after the polymerization reaction is complete, the resulting polymer contains less than about 0.01% residual acrylonitrile. In one embodiment, the resulting polymer contains less than about 0.01%; about 0.001%; about 0.0001%; about 0.00001% residual acrylonitrile, wherein any one of these values can be an upper or a lower limit of the range.

The unreacted monomers can be removed through a steam in a slurry stripper, purging using fluidized beds (diffusion), nitrogen stripping, post-polymerization, devolatilization, or other methods known to one skilled in the arts. Alternatively, unreacted monomers can be removed by treating the resulting polymer with an agent that will react with the remaining unreacted starting material. For example, a polymer made from acrylonitrile can be treated with a thiol compound.

In another embodiment, the thermoplastic material is a copolymer with a lower softening temperature that would expand when exposed to heat from a styling tool, such as, but not limited to a commercial blow-drier, heated brushes (example, T3 Volumizer Heat Brush) hair crimping iron, curling iron, curling wand, hot rollers or other curling implements, rotating hot iron (example, Instyler®) or conventional flat straightening iron), for example, from about 40 to about 230° C.; from about 40 to about 200° C.; from about 40 to about 150° C.; from about 40 to about 100° C.; from about from about 40 to about 50° C. In one embodiment, the thermoplastic material is a copolymer with a lower softening temperature that would expand when exposed to heat from a commercial blow-drier, for example, from about 40 to about 50° C. One of skill in the art would be able to measure the softening temperature based upon known protocols. For example, one of skill in the art could run analysis of thermal transitions using Differential Scanning calorimetry (DSC) to determine the glass transition temperature, or softening temperature of the copolymer. In some embodiments, the copolymer is made from at least one monomer selected from the group consisting of acrylates, methacrylates, styrene, α-methyl styrene, substituted styrene, vinyl acetate, unsaturated dihalides, nitriles, acrylonitriles, and methacrylonitriles. In some embodiments, when the microspheres are made from a copolymer with a lower softening temperature, the microsphere may or may not be expanded prior to inclusion in the present composition. When the microsphere is not expanded prior to combination with the other components of the compositions described herein, heat (for example, with a blow-dryer) can be applied following application of the composition to the hair to volumize the hair. When the microsphere is not expanded prior to combination with the other components of the compositions described herein, the non-expanded microsphere provides initial volume. Applying heat to the hair after application of the composition containing the non-expanded microsphere provides an additional increase in volume as the fluid-filled microsphere expands from exposure to heat.

Microspheres have a mean particle size between about 10 and about 40 or about 10 and about 120 micron. Microspheres with a mean particle size greater than about 40 micron will add volume, but are more easily visible to the naked eye. Microspheres with a mean particle size smaller than 10 micron may also be used to add volume. However, the risk of inhalation exposure in an aerosol application is increased for particle sizes below 10 micron. In one embodiment, the microspheres have a mean particle size of about 15 and 25 micron or about 10 to about 40 micron. In a particular embodiment, the microspheres have a mean particle size of about 20 micron.

The fluid-filled microspheres of the present invention, when in their expanded state, have a low density, between 0.01 g/cm$^3$ and 0.6 g/cm$^3$ depending on the material. In one embodiment, the density is about 0.01 to about 0.07 g/cm$^3$. In one embodiment, the density is about 0.01 to about 0.1 g/cm$^3$; about 0.01 to about 0.05 g/cm$^3$; about 0.01 to about 0.5 g/cm$^3$; about 0.01 to about 0.4 g/cm$^3$; about 0.01 to about 0.3 g/cm$^3$; about 0.01 to about 0.2 g/cm$^3$; about 0.05 to about 0.2 g/cm$^3$; about 0.01 to about 0.09 g/cm$^3$; or about 0.01 to about 0.08 g/cm$^3$.

The fluid-filled microspheres of the present invention, when used without further expansion, have a low density, between 0.01 g/cm$^3$ and 1.2 g/cm$^3$, depending on the material. In one embodiment, the density is about 0.02 to about 0.6 g/cm$^3$. In one embodiment, the density is about 0.01 to about 0.1 g/cm$^3$; about 0.01 to about 0.05 g/cm$^3$; about 0.01 to about 0.5 g/cm$^3$; about 0.01 to about 0.4 g/cm$^3$; about 0.01 to about 0.3 g/cm$^3$; about 0.01 to about 0.2 g/cm$^3$; about 0.05 to about 0.2 g/cm$^3$; about 0.01 to about 0.09 g/cm$^3$; or about 0.01 to about 0.08 g/cm$^3$. In one embodiment, the density is about 0.1 to about 1.2 g/cm$^3$; about 0.2 to about 1.2 g/cm$^3$; about 0.3 to about 1.2 g/cm$^3$; about 0.4 to about 1.2 g/cm$^3$; about 0.5 to about 1.2 g/cm$^3$; about 0.6 to about 1.2 g/cm$^3$; about 0.7 to about 1.2 g/cm$^3$; about 0.8 to about 1.2 g/cm$^3$; about 0.9 to about 1.2 g/cm$^3$; about 1.0 to about 1.2; or about 1.1 to about 1.2.

The composition of the present invention includes insoluble, hollow, fluid-filled microspheres, which is present at a level between 0.01 and 5% of the formula, or between 0.01 and 2% of the formula, preferably from about 0.01 and 2% of the formula, and most preferably from about 0.1% and 0.5% by weight of the composition.

Polymer Fixative:

The hair composition of the present invention includes a polymer fixative (also referred to as a "resin") to facilitate adherence of the microspheres to the surface of the hair. The amount of polymer ranges from 0.1 to 10% by weight of the total composition, preferably from 0.5 to 5% by weight of the total composition.

Any polymer, regardless of charge, that has a film forming or fixative property can be used in the hair composition disclosed herein. A "film forming" or "fixative" property means the polymer is capable of forming, by itself or in the presence of an auxiliary film-forming agent, a continuous film that adheres to a support, such as keratin materials (for example, hair on a person's head). As film former dries, it creates an invisible film and bonds hair strands together at point of contact, or binds another material (for example, a microsphere) to the hair strand. A "hair fixative" is any ingredient which imparts holding or style-retention properties to hair. Any film former or hair fixative can be used in the present formulation. A non-limiting list of examples of such polymers that have a "film forming" or "fixative" property can be found in "Polymers for Personal Care and Cosmetics" ACS Symposium Series, edited by A. Patil and M. Ferritto, August 2014, the teaching of which are herein incorporated by reference.

In some embodiments, polymer fixatives can be nonionic, anionic, or cationic in charge. Examples of anionic polymer fixatives include, but are not limited to, acrylic copolymers like Acrylates/Hydroxyesters Acrylates Copolymer is a copolymer of one or more monomers consisting of acrylic acid, methacrylic acid, or their simple esters, and one or more monomers of hydroxyacrylate esters (Trade name: Acudyne™ 1000 from Dow Chemical); vinyl copolymers like VA/Crotonates/Vinyl Nedoecanoate Copolymer (Trade name: Luviset CAN from BASF) is a polymer formed from vinyl acetate, crotonic acid, and vinyl neodecanoate monomers; Acrylates Copolymer is a copolymer of two or more monomers consisting of acrylic acid, methacrylic acid or one of their simple esters (Trade name: Tilamar® Fix from DSM Nutritionals); polyurethanes such as Polyurethane-1 is a copolymer of isophthalic acid, adipic acid, hexylene glycol, neopentyl glycol, dimethylolpropanoic acid, and isophorone diisocyanate monomers (Trade name: Luviset® P.U.R. from BASF); or blends of the above, such as Polyurethane-14 and AMP-Acrylates Copolymer (Trade Name: DynamX® from Akzo Nobel).

Examples of nonionic polymer fixatives include, but are not limited to, PVP, copolymers of vinylpyrolidone like VP/VA Copolymer (Trade Name: PVP/VA E-335 from Ashland) and Maltodextrin/VP Copolymer (Trade Name: BioStyle CGP™ from Akzo Nobel), acrylic copolymers like Dimethyl Acrylamide/Hydroxyethyl Acrylate/Methoxyethyl Acrylate Copolymer (Trade Name: Plascize L-2700 from Goo Chemical) and Vinyl Caprolactam/VP/Dimethylaminoethyl Methacrylate Copolymer (Trade Name: Advantage® LC-A from Ashland), acrylate copolymers like VP/Vinyl Caprolactam/DMAPA Acrylates Copolymer (Trade Name: Aquaflex™ SF-40 from Ashland).

Examples of cationic polymer fixatives include, but are not limited to, polymeric quaternary ammonium salts like Polyquaternium-69 (Trade Name: Aquastyle™ 300 from Ashland), Polyquaternium-11 (Trade Name: Gafquat® 440 from Ashland), or Polyquaternium-4 (Trade Name: Celquat L®-200 from Akzo Nobel).

Aerosol Propellant:

The present invention includes a propellant at a suitable to deliver the material as a spray. The amount of propellant ranges from about 40 to about 90% or about 55 to about 90% by weight of the total composition, preferably from about 65 to about 85% by weight of the total composition. Examples of suitable propellants include, but are not limited to, Dimethyl Ether (Dymel® A), Difluoroethane (Dymel® 152a), hydrocarbons such as n-butane, isobutane, propane, or combinations of any of the above. Examples of suitable propellants include, but are not limited to, Dimethyl Ether (Dymel® A), Difluoroethane (Dymel® 152a), Tetrafluoroethane (Dymel® 134a), hydrocarbons such as propane, n-butane, isobutane, n-pentane, isopentane, compressed air, carbon dioxide, nitrogen gas, nitrous oxide, or combinations of any of the above.

Optional Components:

Due to the low density of the fluid-filled microspheres, compositions may also include an ingredient to modify the yield of the system to prevent the microspheres from floating to the surface. Ingredients used to modify the yield include, but are not limited to: carbomer and/or other acrylate-based polymers, cationic-based polymers (example: Polyquaternium-37), gums, clays (example: Stearalkonium Hectorite, Benzalkonium Sepiolite, Benzalkonium Montmorillonite, and blends thereof), cellulose derivatives, etc.

Similarly, compositions can be formulated to contain little or no ingredients to modify the yield of the system, recognizing that such compositions will need to be shaken well to redisperse the fluid-filled microspheres before use. An agitator ball may optionally be added to facilitate redispersement of the fluid-filled microspheres.

A preferred optional component in the invention is a conditioning agent selected from volatile and non-volatile emollients, including, but not limited to: fatty alcohols (such as cetyl alcohol); natural oils; butters; silicones; esters; ethers; ceramides; proteins; amino acids; polysaccharides; vitamins such as panthenol and/or its derivatives, ascorbic acid and/or its derivatives; glycols such as glycerin, butylene glycol, propylene glycol, propanediol, or pentylene glycol; polyols such as PEG-8; acids such as aspartic, citric, gluconic, glycolic, lactic, malic, phytic, salicylic, tartaric; bases such as aminomethyl propanol, arginine, sodium hydroxide, triethanolamine, and triisopropanolamine.

Other optional components may include antifoam agents, plasticizing agents, active ingredients, powders for oil absorption, other particles, antioxidants, preservatives, UV inhibitors, fragrance, coloring agents, including dyes and pigments, and buffering agents.

Formulation

In some embodiments of this invention, the hair composition is essentially anhydrous, aerosolized composition. While the present hair composition will deliver a volumizing benefit in aqueous systems and in non-aerosol systems, both aqueous systems and in non-aerosol systems wet the hair significantly on application which "deflates" dry hair, requiring heat, typically from a blow dryer, to dry the product on the hair before a final, voluminous style is achieved. In contrast, the present invention is a hair composition that provides instant volume when applied to dry hair, without the need for application of heat. Hair compositions that are essentially anhydrous and hydro-alcoholic aerosol systems deliver a fine enough spray to not wet or deflate the hair on application. "Essentially anhydrous" means that the final composition comprises less than 1% water.

Methods of Use

The compositions may be used for any cosmetic application. In particular, the compositions are used in a conventional manner for providing hairstyle/hold benefits. An effective amount of the composition is sprayed or applied onto dry or damp hair before and/or after the hair is styled. As used herein "effective amount" means an amount sufficient to provide the hair volume and style performance desired according to the length and texture of the hair. In some embodiments, "hair" does not include eyelashes.

In particular, is a method of volumizing hair of a subject, comprising the steps of applying a composition described herein to the hair; and optionally heating the hair, thereby volumizing the hair. In some embodiments, the composition is applied to dry hair. Alternatively, the hair is wet. In certain embodiments the hair is heated from about 40 to about 230° C. following application of the composition. In particular, the hair is heated from about from about 40 to about 200° C.; from about 40 to about 150° C.; from about 40 to about 100° C.; from about from about 40 to about 50° C. In certain embodiments, the hair is heated with a styling tool, such as, but not limited to a commercial blow-drier, heated brushes, hair crimping iron, curling iron, curling wand, hot rollers or other curling implements, rotating hot iron or conventional flat straightening iron. Methods of measuring the volumizing effect are described below.

In particular, is a method of fixing the hair of a subject, comprising the steps of applying a composition described herein to the hair; and optionally heating the hair, thereby fixing the hair. In some embodiments, the composition is applied to dry hair. Alternatively, the hair is wet. In certain embodiments the hair is heated from about 40 to about 230° C. following application of the composition. In particular, the hair is heated from about from about 40 to about 200° C.; from about 40 to about 150° C.; from about 40 to about 100° C.; from about from about 40 to about 50° C. In certain embodiments, the hair is heated with a styling tool, such as, but not limited to a commercial blow-drier, heated brushes, hair crimping iron, curling iron, curling wand, hot rollers or other curling implements, rotating hot iron or conventional flat straightening iron. Measurement of the fixative properties of the composition can be conducted by methods known to one of skill in the art, for example, the high humidity curl retention test (HHCR test)

Product Form

Compositions of the invention may suitably be in aerosol form. A particularly preferred product form is an aerosol spray. In some embodiments, the product is not in the form of a mascara.

Measurement of Volumizing Effect

The present hair compositions increase the volume of space occupied by the hair of a subject. "Volumizing" means that the amount of space occupied by the subject's hair has been increased. The volumizing effect can be measured either qualitatively or quantitatively. To determine the qualitative effect, the composition can be applied to the hair and either the subject or a skilled technician can be asked to assess the appearance of the hair, and in particular whether a difference between pre-treated and treated hair is seen with regard to the space occupied by the hair or the overall appearance of the hair. Quantitative measurements of increase in volume, which were used for example compositions, can be done using image analysis, for example. A baseline picture of clean, untreated hair is taken using a fixed digital camera. A second image is captured after application of the test product, making sure the head (mannequin or human) is positioned similar to the before image. Before and after photos are compared using photo editing software (examples: Adobe Photoshop, GIMP, etc.). The before image is opened in the software. A mask is created using the selection tool or magnetic lasso, following the border of the hair. Once the hair is masked, the histogram will give the pixel count of the selection. Increase in volume is measured according to the following:

$$\text{volume increase} = \frac{\text{pixel count(treated)} - \text{pixel count(untreated)}}{\text{pixel count(untreated)}} \times 100$$

EXAMPLES

The compositions listed in the following examples illustrate specific embodiments of the compositions of the present invention, but are not intended to be limiting thereof. Other modifications can be undertaken by one skilled in the craft without departing from the spirit and scope of the invention. These examples of the composition of the present invention provide volumizing benefits on the hair.

Example 1

| Ingredient | Supplier | #R-7 Control % w/w | #R-7 % w/w |
|---|---|---|---|
| D.I. Water | N/A | 20.1% | 19.1% |
| Acrylates/C10-30 Alkyl Acrylate Crosspolymer[1] | Lubrizol | 1.0% | 1.0% |
| Denatured Ethanol SDA40B 200 Proof | Pharmco-Aaper | 78% | 78% |
| Acrylonitrile/Methacrylonitrile/Methyl Methacrylate Copolymer microsphere, Water[2] | Akzo Nobel | — | 1.0% |
| Aminomethyl Propanol | Angus Chemical | 0.9% | 0.9% |
| Polyurethane-14, AMP-Acrylates Copolymer[4] | Akzo Nobel | 3.0% | 3.0% |
| | TOTAL | 100.0% | 100.0% |

[1]Commercially available as Carbopol ® Ultrez 21 polymer from Lubrizol.
[2]Commercially available as EXPANCEL ® 920 WEP 40 d24 from Akzo Nobel.
[3] Commercially available as AMP Ultra ™ PC-2000 from Angus Chemical.
[4]Commercially available as DynamX ® from Akzo Nobel.

Sift Acrylates/C10-30 Alkyl Acrylate Crosspolymer ("polymer") onto the surface of still D.I. Water. Allow polymer to wet out completely. Begin mixing. Add Ethanol. Mix until uniform. Add microsphere and mix until uniformly dispersed. Neutralize with Aminomethyl Propanol. Add Polyurethane-14, AMP-Acrylates Copolymer ("resin blend"). Mix until uniform. Adjust batch to total weight with additional ethanol to account for any evaporative loss during mixing.

Hair on a mannequin head was parted down the center. Test product from above was applied to each half of the mannequin head as follows:

| | |
|---|---|
| Mannequin's left side | 10.49-grams of #R-7 Control |
| Mannequin's right side | 10.48-grams of #R-7 |

Product was combed through to ensure even distribution and dried with a blow drier on high because the product wet the hair. As seen in FIG. 1, formula #R-7, which contained the microspheres, added more volume than the #R-7 Control on the left.

Example 2

| Ingredient | Supplier | #R-96 % w/w |
|---|---|---|
| Denatured Ethanol SDA40B 200 Proof | Pharmco-Aaper | 11.890% |
| VP/VA Copolymer, 50% solution in ethanol[1] | Ashland | 5.000% |
| D.I. Water (Water) | — | 0.576% |
| Octafluoropentyl Methacrylate | Central Glass Germany | 0.420% |
| Fragrance | Sozio | 0.400% |
| Acrylonitrile/Methacrylonitrile/Methyl Methacrylate Copolymer microsphere[3] | Akzo Nobel | 0.313% |
| Aluminum Starch Octenylsuccinate, Acrylates Copolymer, Magnesium Carbonate[4] | Akzo Nobel | 0.313% |
| Zeolite[5] | Honeywell | 0.125% |
| Hydrofluorocarbon 152a[6] | Dupont | 42.593% |
| Dimethyl Ether | Dupont | 38.372% |
| | TOTAL | 100.000% |

[1]Commercially available as PVP/VA E-335 from Ashland.
[2] Commercially available as Fragrance Sozio SZ-80580.
[3]Commercially available as EXPANCEL ® 920 DU 80 from Akzo Nobel.
[4]Commercially available as Natrasorb ® HFB from Akzo Nobel.
[5]Commercially available as Asensa ® DS912 from Honeywell.
[6]Commercially available as Dymel ® 152a propellant from Dupont.
[7] Commercially available as Dymel ® A propellant from Dupont.

Charge vessel with ethanol. Add VP/VA copolymer and mix until uniform. Add the next six ingredients (up to and including Zeolite), in order, mixing well between each addition. Fill aerosol cans with concentrate and charge with appropriate amounts of the two propellants.

Figure 2:
FIG. 2 is a photograph of mannequin head before application of a hair composition (Left, "before") and a photograph of a mannequin head onto which a composition of the invention was applied to the right side of the mannequin's head and the left side of the mannequin's head was left untreated (Right, "after").

Hair on a clean, dry mannequin head was parted down the center. 25-grams of test product from above was applied to the right side of the mannequin head. Left was untreated. FIG. 2 shows photographs taken before and after application to illustrate change in volume. The increase in volume for both the treated and untreated sides was calculated as described above. Results are listed below:

% increase(treated)=56.1%
% increase(untreated)=7.7%

Example 3

| Ingredient | Supplier | #R-97 % w/w |
|---|---|---|
| Denatured Ethanol SDA40B 200 Proof | Pharmco-Aaper | 11.890% |
| VP/VA Copolymer, 50% solution in ethanol[1] | Ashland | 5.000% |
| D.I. Water (Water) | — | 0.576% |
| Octafluoropentyl Methacrylate | Central Glass Germany | 0.420% |
| Fragrance | Sozio | 0.400% |
| Acrylonitrile/Methacrylonitrile/Methyl Methacrylate Copolymer microsphere3[5] | Akzo Nobel | 0.313% |
| Aluminum Starch Octenylsuccinate, Acrylates Copolymer, Magnesium Carbonate[4] | Akzo Nobel | 0.313% |
| Zeolite[5] | Honeywell | 0.125% |
| Hydrofluorocarbon 152a[6] | Dupont | 42.593% |
| Dimethyl Ether[7] | Dupont | 38.372% |
| TOTAL | | 100.000% |

[1]Commercially available as PVP/VA E-335 from Ashland.
[2] Commercially available as Fragrance Sozio SZ-80580.
[3] Commercially available as EXPANCEL ® 920 DE 40 from Akzo Nobel.
[4]Commercially available as Natrasorb ® HFB from Akzo Nobel.
[5]Commercially available as Asensa ® DS912 from Honeywell.
[6]Commercially available as Dymel ® 152a propellant from Dupont.
[7]Commercially available as Dymel ® A propellant from Dupont Charge vessel with ethanol. Add VP/VA copolymer and mix until uniform. Add the next six ingredients (up to and including Zeolite), in order, mixing well between each addition. Fill aerosol cans with concentrate and charge with appropriate amounts of the two propellants.

Figure 3:
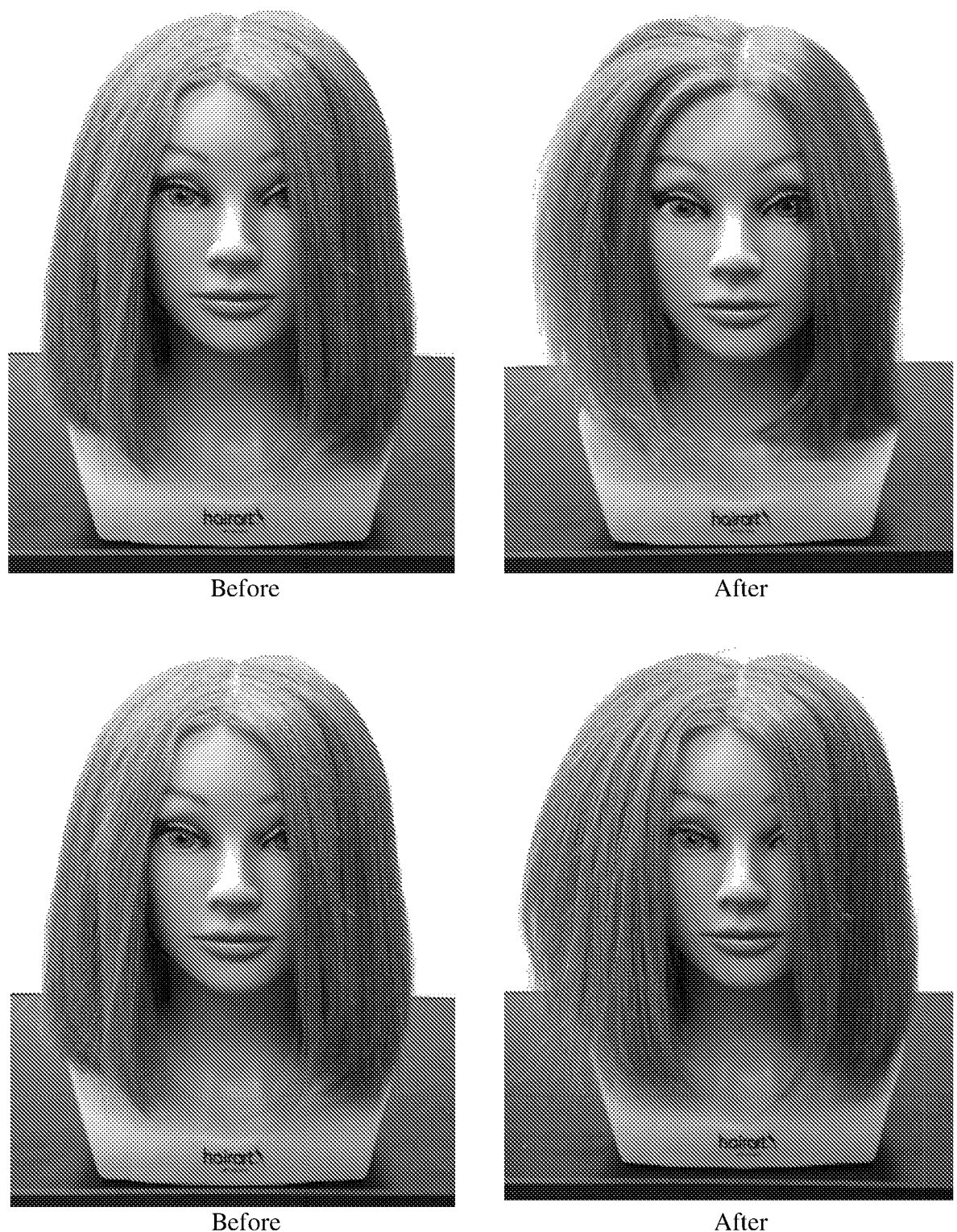
FIG. 3 is a photograph of mannequin head before application of a hair composition (Left, "before") and a photograph of a mannequin head onto which a composition of the invention was applied to the right side of the mannequin's head and the left side of the mannequin's head was left untreated (Right, "after").

Hair on a clean, dry mannequin head was parted down the center. 25-grams of test product from above was applied to the right side of the mannequin head. Left was untreated. FIG. 3 shows photographs taken before and after application to illustrate change in volume. The increase in volume for both the treated and untreated sides was calculated as described above. Results are listed below:

% increase(treated)=20.86%

% increase(untreated)=−14.37%

The experiment was repeated to show reproducibility. The increase in volume for both the treated and untreated sides was calculated as described above. Results are listed below:

% increase(treated)=52.76%

% increase(untreated)=13%

Example 4

| Ingredient | Supplier | #R-130A % w/w | #R-130B % w/w |
|---|---|---|---|
| Denatured Ethanol SDA40B 200 Proof | Pharmco-Aaper | 13.075% | 13.075% |
| Benzalkonium Sepiolite, Benzalkonium Montmorillonite[1] | Lubrizol | 0.175% | 0.175% |
| VP/VA Copolymer, 50% solution in ethanol[2] | Ashland | 5.0% | 5.0% |
| D.I. Water (Water) | — | 0.5% | 0.5% |
| Octafluoropentyl Methacrylate | Central Glass Germany | 0.1% | 0.1% |
| Fragrance[3] | Sozio | 0.4% | 0.4% |
| Calcium Aluminum Borosilicate, Silica[4] | Sensient LCW | 0.3125% | — |
| Acrylonitrile/Methyl Methacrylate Copolymer, Butane, Magnesium Hydroxide[5] | Akzo Nobel | — | 0.3125% |
| Aluminum Starch Octenylsuccinate, Acrylates Copolymer, Magnesium Carbonate[6] | Akzo Nobel | 0.313% | 0.3125% |
| Zeolite[7] | Honeywell | 0.125% | 0.125% |
| Hydrofluorocarbon 152a[8] | Dupont | 80.0% | 80.0% |
| TOTAL | | 100.0% | 100.0% |

[1]Commercially available as Garamite 7305 from Byk Additives
[2]Commercially available as PVP/VA E-335 from Ashland.
[3]Commercially available as Fragrance Sozio SZ-80580.
[4]Commercially available as Natpure Hollowbead.
[5]Commercially available as EXPANCEL ® FG52 DU 80 from Akzo Nobel.
[6]Commercially available as Natrasorb ® HFB from Akzo Nobel.
[7]Commercially available as Asensa ® DS912 from Honeywell.
[8]Commercially available as Dymel ® 152a propellant from Dupont.

Charge vessel with ethanol. Add Garamite, mix until dispersed. Add VP/VA copolymer and mix until uniform. Add the next six ingredients (up to and including Zeolite), in order, mixing well between each addition. Fill aerosol cans with concentrate and charge with appropriate amounts of propellant.

Hair on test panelists was parted down the center. Control product (#R-130A) from above was applied to the left side of the panelist's head. Test product (#R-130B) from above was applied to the right side of the panelist's head. Aerosol cans were weighted before and after application to ensure equal amounts of test and control product were applied to each side. Hair stylists trained to assess hair for differences evaluated the results. Stylists noticed more volume and lift at the hair root near the scalp provided by the test product versus the control. Additionally, stylists noticed an increase in the width of the hair as measured near the cheekbones.

The invention claimed is:

1. A hair treatment composition comprising
    at least one monohydric alcohol having 1 to 6 carbon atoms;
    hollow, fluid-filled microspheres, wherein the microspheres are present at a level of 0.01% to 2.0% by weight of the composition, have a mean particle size of 10 to 40 micron, and have a density of 0.01 g/cm$^3$ to about 0.6 g/cm$^3$ in the expanded state;
    at least one polymer fixative present at a level of 0.1% to 10% by weight of the composition; and
    at least one propellant present at a level of 65% to 85% by weight of the composition, wherein the composition is essentially anhydrous.

2. A hair treatment composition packaged in an aerosol device comprising
    at least one monohydric alcohol having 1 to 6 carbon atoms;
    hollow, fluid-filled microspheres, wherein the microspheres are present at a level of 0.01% to 2.0% by weight of the composition, have a mean particle size of 10 to 40 micron, and have a density of 0.01 g/cm$^3$ to about 0.6 g/cm$^3$ in the expanded state;
    at least one polymer fixative present at a level of 0.1% to 10% by weight of the composition; and
    at least one propellant present at a level of 65% to 85% by weight of the composition, wherein the composition is essentially anhydrous.

3. The composition of claim 1, wherein the monohydric alcohol is selected from ethanol and isopropyl alcohol.

4. The composition of claim 1, wherein the monohydric alcohol is present at a level from about 2% to about 20% of the composition.

5. The composition of claim 1, wherein the microspheres comprise a thermoplastic material wall.

6. The composition of claim 5, wherein the thermoplastic material is a polymer or copolymer of at least one monomer selected from the group consisting of acrylates, methacrylates, styrene, substituted styrene, unsaturated dihalides, acrylonitriles, methacrylonitriles, vinyl and vinyl chloride.

7. The composition of claim 6, wherein the polymer or copolymer is essentially free of one or more residual starting materials.

8. The composition of claim 7, wherein the polymer or copolymer comprises less than about 0.01% of one or more residual starting materials.

9. The composition of claim 5, wherein the thermoplastic material is a acrylonitrile/methyl methacrylate/vinylidene chloride copolymer.

10. The composition of claim 5, wherein the thermoplastic material is a acrylonitrile/methacrylonitrile/methyl methacrylate copolymer.

11. The composition of claim 9 or 10, wherein the copolymer is essentially free of unreacted acrylonitrile.

12. The composition of claim 9 or 10, wherein the copolymer comprises less than about 0.01% unreacted acrylonitrile.

13. The composition of claim 1, wherein the microspheres have a mean particle size of about 20 micron.

14. The composition of claim 1, wherein the microspheres are present at a level of about 0.1 to about 0.5% of the composition.

15. The composition of claim 1, wherein the polymer fixative is present at a level of about 0.5 to 5% by weight of composition.

16. The composition of claim 1, wherein the polymer fixative is nonionic, anionic, or cationic in charge.

17. The composition of claim 1, wherein the propellant is selected from the group consisting of dimethyl ether, difluoroethane, tetrafluoroethane, propane, n-butane, isobutane, n-pentane, isopentane, compressed air, carbon dioxide, nitrogen gas, nitrous oxide, and combinations thereof.

18. A method of volumizing hair of a subject, comprising the steps of applying a composition of claim 1 to the hair; and optionally heating the hair, thereby volumizing the hair.

19. The method of claim 18, wherein the composition is applied to dry hair.

20. The method of claim 18, wherein the hair is heated from about 40 to about 230° C.

21. The method of claim 18, wherein the hair is heated with a styling tool.

* * * * *